US008673878B2

(12) United States Patent
Taylor et al.

(10) Patent No.: US 8,673,878 B2
(45) Date of Patent: *Mar. 18, 2014

(54) MUCOSAL TREATMENT

(75) Inventors: Catherine Taylor, Trondheim (NO); Kurt Ingar Draget, Trondheim (NO); Olav Asmund Smidsrod, Trondheim (NO)

(73) Assignee: NTNU Technology Transfer AS, Trondheim (NO)

( * ) Notice: Subject to any disclaimer, the term of this patent is extended or adjusted under 35 U.S.C. 154(b) by 852 days.

This patent is subject to a terminal disclaimer.

(21) Appl. No.: 12/089,530

(22) PCT Filed: Oct. 6, 2006

(86) PCT No.: PCT/GB2006/003732
§ 371 (c)(1),
(2), (4) Date: Oct. 9, 2008

(87) PCT Pub. No.: WO2007/039760
PCT Pub. Date: Apr. 12, 2007

(65) Prior Publication Data
US 2009/0156549 A1 Jun. 18, 2009

(30) Foreign Application Priority Data

Oct. 6, 2005 (GB) .................................. 0520375.7

(51) Int. Cl.
*A01N 43/04* (2006.01)
*A61K 31/715* (2006.01)

(52) U.S. Cl.
USPC .............................................. 514/54; 514/61

(58) Field of Classification Search
None
See application file for complete search history.

(56) References Cited

U.S. PATENT DOCUMENTS

| | | | |
|---|---|---|---|
| 4,225,592 A | 9/1980 | Lakatos et al. | |
| 5,166,137 A | 11/1992 | Otterlei et al. | |
| 5,459,054 A | 10/1995 | Skjak-Braek et al. | |
| 5,460,957 A * | 10/1995 | Hiura et al. | 435/100 |
| 5,683,991 A | 11/1997 | Guggenbichler et al. | |
| 5,759,572 A | 6/1998 | Sugimoto et al. | |
| 5,795,587 A | 8/1998 | Gao et al. | |
| 6,121,441 A | 9/2000 | Simensen et al. | |
| 6,339,075 B1 | 1/2002 | King et al. | |
| 6,407,226 B1 | 6/2002 | Simensen et al. | |
| 6,440,413 B1 * | 8/2002 | Hooreman | 424/94.63 |
| 6,747,015 B2 * | 6/2004 | Byon et al. | 514/54 |
| 2003/0013678 A1 | 1/2003 | Lang et al. | |
| 2003/0022863 A1 | 1/2003 | Stahl et al. | |
| 2003/0059474 A1 | 3/2003 | Scott et al. | |
| 2003/0224070 A1 | 12/2003 | Sweazy et al. | |
| 2004/0073964 A1 | 4/2004 | Ellington et al. | |
| 2004/0224922 A1 | 11/2004 | King | |
| 2005/0158392 A1 | 7/2005 | Kim et al. | |
| 2006/0083780 A1 | 4/2006 | Heyes et al. | |
| 2009/0010914 A1 | 1/2009 | Taylor et al. | |

FOREIGN PATENT DOCUMENTS

| | | |
|---|---|---|
| CA | 2 428 473 A1 | 5/2002 |
| DE | 268865 A1 | 6/1989 |
| DE | 19520743 A1 | 12/1996 |
| EP | 324720 A1 | 7/1989 |
| EP | 506325 A1 | 9/1992 |
| EP | 0888778 A1 | 1/1999 |
| EP | 1234584 | 8/2002 |
| EP | 1714660 A1 | 10/2006 |
| EP | 1745705 A1 | 1/2007 |
| EP | 1837018 A1 | 9/2007 |
| FR | 7576 M | 1/1970 |
| GB | 1042379 A | 9/1966 |
| GB | 2 430 881 A1 | 4/2007 |
| JP | 61-076413 | 4/1986 |
| JP | 01-197431 | 8/1989 |
| JP | 09208472 A | 8/1997 |
| JP | 2000-034302 | 2/2000 |
| JP | 2002-338493 A | 11/2002 |
| JP | 2005-145885 | 6/2005 |
| JP | 2006-028041 | 2/2006 |
| WO | WO 88/09794 A1 | 12/1988 |
| WO | WO 91/07951 A1 | 6/1991 |
| WO | WO 91/11205 A1 | 8/1991 |
| WO | WO 95/18145 A1 | 7/1995 |
| WO | WO 98/13024 A2 | 4/1998 |
| WO | WO 01/15672 A2 | 3/2001 |
| WO | WO 01/17506 A1 | 3/2001 |
| WO | WO 01/66084 A2 | 9/2001 |
| WO | WO 01/72278 A2 | 10/2001 |
| WO | WO 2007/02224 A2 | 1/2004 |
| WO | WO 2005/089722 A1 | 9/2005 |
| WO | WO 2007/02224 A2 | 1/2007 |
| WO | WO 2007/039754 A1 | 4/2007 |
| WO | WO 2007/039760 A2 | 4/2007 |
| WO | WO 2007/046719 A2 | 4/2007 |

(Continued)

OTHER PUBLICATIONS

Terada et al. Microbial Ecology in Health and Disease vol. 8: 259-266 (1995).*
Tadashi et al. Japanese Journal of Nutrition and Dietetics, vol. 60, No. 3, pp. 137-143 (2002), abstract only.*
Akiyama et al. Biosci. Biotech. Biochem., 56 (2), 355-356, 1992.*
Pandey et al. Handbook of Carbohydrate Engineering, May 2005, Chapter 27, pp. 799-815.*
Eiselt et al. Biomaterials (2000) 1921-1927.*
Shadrawi et al. Gut 2002; 51: 285-286.*
Shraishi et al. J. Pharm. Pharmacol. 1991, 43: 615-620.*
Ikeda et al. (Carbohydrate Polymers 42 (2000) 421-425.*
FMC BioPolymer, Alginates brochure, 2003.*

(Continued)

*Primary Examiner* — Layla Bland
(74) *Attorney, Agent, or Firm* — Knobbe Martens Olson & Bear, LLP

(57) ABSTRACT

The invention provides a method of treatment of a female human or non-human subject to enhance cervical mucus penetrability by spermatozoa, which method comprises vaginally applying to said subject an effective amount of a spermicide-free, physiologically tolerable oligouronate.

10 Claims, 3 Drawing Sheets

(56) References Cited

FOREIGN PATENT DOCUMENTS

| WO | WO 2008/125828 A2 | 10/2008 |
| WO | WO 2008/137114 A1 | 11/2008 |
| WO | WO 2009/142892 A2 | 11/2009 |

OTHER PUBLICATIONS

Banning D. et al. 1997 "Oscillatory and thermorheological characterization of alginate/mucin mixes" Pharmacy and Pharmacology (British Pharmaceutical Conference 1997 Science proceedings 134$^{th}$ meeting, Scarborough, Sep. 15-18, 1997, Abstract 65.

Murata, K. et al. 1992 "Continuous depolymerization of alginates by a non-support bioreactor system containing flocculated bacterial cells" *Journal of Fermentation and Bioengineering* 73:172-174.

Tang, J.X. et al. 2005 "Anionic poly(amino acid)s dissolve F-actin and DNA bundles, enhance DNase activity, and reduce the viscosity of cystic fibrosis sputum" *Am J Physiol Lung Cell Mol Physiol* 289:L599-L605.

Chono, S. et al. 2008 "An efficient and low immunostimulatory nanoparticle formulation for systemic siRNA delivery to the tumor" *Journal of Controlled Release* 131: 64-69.

Dalby, B. et al. 2004 "Advanced transfection with Lipofectamine 2000 reagent: primary neurons, siRNA, and high-throughput applications" *Methods* 33: 95-103.

Fiel, Stanley B. et al. (1995) "Comparison of Three Jet Nebulizer Aerosol Delivery Systems Used to Administer Recombinant Human DNase I to Patients With Cystic Fibrosis" *CHEST Official Publication of the American College of chest Physicians* 108: 153-156.

Jiang, G. et al. 2007 "DNA/PEI/Alginate polyplex as an efficient in vivo gene delivery system" *Biotechnology and Bioprocessing Engineering* 12: 684-689.

Klöck, G. et al. 1997 "Biocompatibility of mannuronic acid-rich alginates" *Biomaterials* 18: 707-713.

Kong, H. J. et al. 2008 "Design of Biodegradable Hydrogel for the Local and Sustained Delivery of Angiogenic Plasmid DNA" *Pharaceutical Research* 25: 1230-1238.

Krebs, M. D. et al. 2009 "Localized and Sustained Delivery of Silencing RNA from Macroscope Biopolymer Hydrogels" *Journal of the American Chemical Society* 131: 9204-9206.

Rakkhithawatthana, V. et al. 2010 "Investigation of gene transferring efficacy through nano-polyplex consisting of methylated N-(4-pyridinylmethyl) chitosan chloride and poly(ethylenimine) in human cell lines" *Carbohydrate Polymers* 80: 276-284.

Sioud, M. et al. 2003 "Cationic liposome-mediated delivery of siRNAS in adult mice" *Biochemical and Biophysical Research Communications* 312: 1220-1225.

Yun, Y. H. et al. 2004 "Hyaluronan microspheres for sustained gene delivery and site-specific targeting" *Biomaterials* 25: 147-157.

Westedt, U. et al. 2007 "Poly(vinylalcohol)-graft-poly(lactide-co-glycolide) nanoparticles for local delivery of paclitaxel for restenosis treatment" *Journal of Controlled Release* 119: 41-51.

Iwamoto, M. et al. 2005 "Structure-activity relationship of alginate oligosaccharides in the induction of cytokine production from RAW264.7 cells" *FEBS Letters* 579: 4423-4429.

Witschi, C. et al. 1999 "In vitro evaluation of microparticles and polymer gels for use as nasal platforms for protein delivery" *Pharmaceutical Research* 16: 382-390.

Hanninen, A. and Harrison, L.C. 2004 "Mucosal Tolerance to Prevent Type 1 Diabetes: Can the Outcome Be Improved in Humans?" *Rev Diabet Stud* 1: 113-121.

Merck Manual, "Disorders," www.merckmanuals.com/professional/index.html, accessed Aug. 6, 2012.

Merck Manual, "Diseases," www.merckmanuals.com/professional/index.html, accessed Aug. 6, 2012.

Merck Manual, "Diabetes," www.merckmanuals.com/professional/index.html, accessed Aug. 6, 2012.

Grasdalen, H. et al. 1979 "A.P.M.R. study of the composition and sequence of urinate residues in alginates" *Carbohydrate Research* 68: 23-31.

\* cited by examiner

MUCOSAL TREATMENT

This application is U.S. National Phase of International Application PCT/GB2006/003732, filed Oct. 6, 2006 designating the U.S., and published in English as WO 2007/039760 on Apr. 12, 2007, which claims priority to Great Britain Patent Application No. 0520375.7 filed Oct. 6, 2005.

This invention relates to a method of treatment of human or non-human animals, in particular mammals, to combat elevated mucosal viscosity in the reproductive or digestive tracts, e.g. to facilitate fertilization or fecal clearance, e.g. to enhance mucosal penetrability by spermatozoa (sperm), or to combat constipation.

Cervical mucus, produced by the glands of the uterine cervix, is a heterogeneous entity containing different types of secretions in different proportions throughout the menstrual cycle. The nature of the secretion is such that it provides a barrier to sperm migration through the cervix at all times except during the "fertile window" when ovulation is occurring and conception is possible. This acts to protect the uterus, fallopian tubes and ovaries from unnecessary exposure to pathogens.

In order to support sperm migration during the fertile window, the cervical mucus must have appropriate biochemical and biophysical characteristics. Biochemical properties, such as pH and osmolarity are important in providing appropriate conditions for sperm survival (see Marriott et al., "Mucus physiology and pathology" in Bioadhesive Drug Delivery Systems, CRC Press, 1990), while the biophysical properties, such as rheology and macromolecular network morphology, affect the motility of sperm within the mucus (see Rutllant et al., Reprod. Dom. Anim. 40: 79-86 (2005)).

Clinically, the fertile window may be identified by detecting the surge in lutenising hormone before ovulation and the rise in basal body temperature after ovulation and by examining the biophysical properties of the cervical mucus in particular its spinnbarkeit (spinnability), which is essentially a measure of how stretchy the mucus is and as such is related to the rheology of the mucus. Cervical mucus ferning, i.e. the crystallisation patterns that form when mucus from the ovulatory period is allowed to air dry, has also been shown to be related to the morphology of the macromolecular network within the mucus (see Menarguez et al., Human Reproduction 18: 1782-1789 (2003)).

The ferning patterns of mucus (and hence the macromolecular network morphology) have been shown to be a significant factor in the chance of achieving a pregnancy with the use of artificial insemination and for a subset of women, "problem mucus" appears to be a major barrier to achieving pregnancy (see Boyers et al., Human Reproduction 6: 1108-1114 (1991)).

There is therefore a need for a method of modulating the biophysical properties of cervical mucus for optimum sperm motility, not just for women with "problem mucus" but for any woman who wishes to maximise her chances of conceiving, and also for animal breeders who wish to maximise the chance of pregnancy in their animals.

We have now found that oligouronates (in particular ones containing two to thirty monomer residues) can modify the morphology of the macromolecular network of cervical mucus so as to cause it to resemble mucus during the ovulatory phase, i.e. so as to enhance its penetrability by sperm.

Thus viewed from one aspect the invention provides a method of treatment of a female human or non-human (e.g. mammalian) subject to enhance cervical mucus penetrability by spermatozoa, e.g. to enhance the likelihood of pregnancy post-vaginal insemination by natural or artificial means, which method comprises vaginally applying to said subject an effective amount of a spermicide-free, physiologically tolerable oligouronate.

Viewed from a further aspect the invention provides the use of an oligouronate, for the manufacture of a medicament for vaginal application to enhance cervical mucus permeability to spermatozoa.

In this method of the invention, the oligouronate is preferably applied in the form of a sterile aqueous composition, e.g. a solution, gel, emulsion, cream or paste, or as a tablet, capsule or vaginal suppository. Such compositions, which form a further aspect of the present invention, may if desired contain further agents to enhance sperm function, e.g. pH regulators, and antioxidants, or to assist insemination, e.g. muscle relaxants, lubricants, etc.

Thus viewed from a further aspect the invention provides a sterile, spermicide-free vaginal treatment composition comprising a physiologically tolerable carrier or excipient together with an oligouronate and a pH regulator, optionally further comprising an agent selected from the group consisting of antioxidants and lubricants.

Clearly the compositions may also contain further physiologically tolerable pharmaceutical or cosmetic components such as are normally found in compositions for vaginal application, e.g. binders, diluents, soluble capsule shells, fragrances, antibiotics, vitamins, oils, emulsifiers, suppository bases, etc.

The oligouronate will preferably be present as about 0.1 to 2.5 g per dosage unit, more preferably 0.5 to 2 g/dosage unit for an adult human female. Dosages for other species may be calculated analogously by reference to average body size, e.g. [(0.1 to 2.5)/60] g/dosage unit/kg bodyweight, etc.

The composition is preferably applied in advance of insemination, e.g. 1 to 60 hours beforehand, preferably 2 to 48 hours beforehand, especially 4 to 36, e.g. 20 to 52 hours beforehand. This may be achieved for example by vaginal douche, by vaginal insertion of a water-degradable tablet or capsule, or by injection of a gel or paste. The timing of application may be selected by monitoring parameters indicative of ovulation or proximity of ovulation, e.g. temperature.

If desired, the composition may be applied two or more times, e.g. well in advance of insemination and shortly before (e.g. within 1 hour of) insemination.

Where a pH regulator is included in the composition, this is preferably such as to cause the vaginal pH to become slightly basic, e.g. pH 7.1 to 7.6, especially about pH 7.4. Routine physiologically tolerable buffers may be used in this regard.

The female treated according to the method of the invention is preferably a human female, in particular one diagnosed as having fertility problems due to problematic mucus. The method however may be used by other female humans of an age capable of becoming pregnant in order to increase the chance of pregnancy. It may also be used by vets and animal breeders, e.g. farmers, for animals such as cows, horses, dogs, cats, sheep, goats, pigs, etc.

The compositions of the invention are preferably packaged together with instructions for use in the method of the invention, particularly preferably in dosage unit form, and especially preferably together with an applicator, e.g. a syringe. The use of pre-loaded syringes is especially preferred. Alternatively the applicator may take the form of a cervical diaphragm, loaded on the concave side with the composition, to be removed before insemination unless the diaphragm membrane is of a sperm-permeable or water-soluble material. Such syringes and diaphragms form further aspects of the present invention.

In the treatment of cervical mucus, polysaccharides containing in their polymer structure blocks of uronic acid residues, e.g. alginates, may be used in place of oligouronates and such use is deemed to fall within the scope of the invention.

Treatment of cervical mucus is only one aspect of the present invention. It is also particularly suited to the treatment of constipation, a problem faced particularly by sufferers of cystic fibrosis.

Cystic fibrosis is the most common lethal genetic disease in European populations. The disease is caused by a mutation in the gene that codes for the cystic fibrosis transmembrane regulator (CFTR), a chloride channel that is present in secretary and other cells in the body. The disease is characterized by the presence of thick, intractable mucus secretions in the body that can lead to lung disease, sinusitis, digestive problems and infertility. The normal pattern of mucociliary clearance in the lungs fails to clear the unduly viscous mucus which becomes colonized by microorganisms, which in turn increases mucus viscosity and may lead to chronic lung inflammation and obstruction. Lung disease is thus the biggest health problem for the majority of CF patients and is the major cause of death.

Mucus is a normal secretion of the entire respiratory tract, including the lungs. Its primary function is as part of the mucociliary clearance system that keeps the lungs clean and protects against infection. The mucociliary clearance system has three main components: mucus; cilia; and the airway surface liquid. The epithelial surface thus comprises mucus secreting goblet cells and ciliated epithelial cells with an overlying layer of airway surface liquid and above that a layer of mucus, into which the tips of the cilia protrude. The mucus is a sticky gel material composed primarily of water (about 95% wt.) and mucins, gel forming molecules responsible for the physical properties of the mucus. The cilia are small hair-like projections from the surface of the epithelial cells, which beat rhythmically in the watery, non-viscous airway surface liquid with their tips immersed in the mucus layer. The mucus layer forms a sticky blanket on the lung surface that traps bacteria, viruses, inhaled particles, environmental pollutants and cell debris. The beating of the cilia serves to propel this mucus blanket and anything trapped in it towards the mouth and out of the lungs. Under normal conditions, the mucociliary clearance system functions effectively and the lungs are kept clean and free of infection. If the system is overwhelmed, there is a second line of defence—cough. Thus when increased levels of mucus are secreted in response to irritation or inflammation, e.g. due to inhaled particles or infection, the mucus is projected out of the lungs by the cough reflex.

In CF patients the mucus in the lung is thicker and more viscous than normal, and this thicker mucus is not so easily transported by the cilia. As a result the mucociliary clearance system is compromised and the lungs are more vulnerable to infection. In addition, the lungs of CF patients appear to be in a hyper-inflammatory state with a continual low level of inflammation and a heightened response to agents that normally cause inflammation. This is problematic as part of the response to inflammation is increased production of mucus. The increased mucus builds up if it is too thick to be cleared by the mucociliary clearance system or coughing, lung capacity is reduced and the exchange of oxygen across the mucosa is decreased. This provides an ideal environment for bacterial colonization, a serious problem for CF patients as it also causes inflammation and activates the immune response. This leads not only to increased mucus secretion but also an increased presence of immune response cells and agents such as macrophages and lysozymes. As bacteria and macrophages die, their cell contents are released into the mucus and these include viscous molecules such as DNA. Furthermore, some of the bacteria, e.g. *Burkholderia* sp. and *Pseudomonas aeruginosa*, also secrete highly viscous polysaccharides, in the latter case alginates. These molecules further increase the viscosity of the mucus, in the case of the alginates apparently by interaction with the mucin matrix of the mucus but in the case of DNA apparently by increasing the viscosity of the sol phase within the mucin matrix.

Maintaining the mucus in a form capable of being transported by the cilia is thus a key goal of treatment of CF. Agents which simply break down its gel-like structure would result in fluid which was as untransportable as the hyperviscous mucus of the CF patient. It is important therefore that any treatment agent should not break down the gel matrix formed by the glycoprotein mucins.

We have found that this can be achieved using an oligouronate, in particular one containing two to thirty monomer residues.

CF patients, especially infants, and the elderly in general, suffer particularly from constipation. By reducing mucosal hyperviscosity in the gut using oligouronates according to the invention, this problem also may be addressed.

Thus, viewed from one aspect the invention provides a method of treatment of a human or non-human (e.g. mammalian) subject to combat mucosal hyperviscosity, e.g. in the digestive, respiratory (such as in the case of COPD—chronic obstructive pulmonary disease) or reproductive tracts, e.g. to treat cystic fibrosis patients, to combat constipation, to combat sinusitis or other nasal congestion, or to enhance fertility, which method comprises application to a mucosal surface in a said tract in said subject of an effective amount of a physiologically tolerable oligouronate.

Viewed from a further aspect the invention provides the use of a physiologically tolerable oligouronate for the manufacture of a medicament for use in the treatment of mucosal hyperviscosity.

The application of the oligouronate may be by any means which delivers it to a mucus secreting, or mucus carrying surface in the patient's body, e.g. in the female reproductive system or the gastrointestinal tract, or the respiratory tract, e.g. the lungs. In the case of the airway, introduction will typically be by inhalation, e.g. of liquid droplets (for example an aerosol) or a powder. In the case of the female reproductive system, as discussed above, introduction will generally be by injection, e.g. into the vagina or the womb, generally of a solution, suspension or dispersion of the oligoelectrolyte. In the case of treatment of the gut, introduction may be oral or rectal, for example of solutions, suspensions, dispersions, syrups, powders, tablets, coated tablets, capsules or suppositories. Where constipation is to be combatted, the oligouronate may be used as a food additive or supplement or may be present in a vitamin or mineral pill. Viewed from a further aspect therefore the invention provides a foodstuff or food additive comprising a nutrient material, e.g. a material containing protein and/or carbohydrate, and a physiologically tolerable oligouronate.

The counterions for the oligouronate may be any of the physiologically tolerable ions commonly used for charged drug substances, e.g. sodium, potassium, ammonium, chloride, mesylate, meglumine, etc. Ions which promote alginate gelation, e.g. group 2 metals, however will preferably not be used.

While the oligouronate may be a synthetic material, it is preferably a derivative, having a weight average molecular weight of less than 100000 Da, of a naturally occurring polysaccharide. It is preferably a 3- to 28-mer, in particular a 4- to 25-mer, especially a 6- to 22-mer, in particular an 8- to 15-mer, especially a 10-mer, e.g. having a molecular weight in the range 350 to 6000 Da especially 750 to 4500 Da. It may be a single compound or it may be a mixture of oligouronates, e.g. of a range of degrees of polymerization. Moreover, the monomeric residues in the oligouronate, i.e. the monosaccharide groups, may be the same or different.

Oligouronates are readily accessible from natural sources since many natural polysaccharides contain uronic acid residues such as guluronic and galacturonic acid residues.

Polysaccharide to oligosaccharide cleavage to produce oligouronates useable according to the present invention may be performed using conventional polysaccharide lysis techniques such as enzymatic digestion and acid hydrolysis. Oligouronates may then be separated from the polysaccharide breakdown products chromatographically using an ion exchange resin or by fractionated precipitation or solubilization.

Examples of polysaccharides containing uronates include naturally occurring polysaccharides (such as xanthan, pectin, alginates, hyaluronan, heparin and chondroitin sulphate.) and chemically modified polysaccharides, including but not limited to polysaccharides modified to add charged groups (such as carboxylated or carboxymethylated glycans), and polysaccharides modified to alter flexibility (e.g. by periodate oxidation). Suitable polysaccharides are discussed for example in "Handbook of Hydrocolloids", Ed. Phillips and Williams, CRC, Boca Raton, Fla., USA, 2000. The use of alginates however is especially preferred as these naturally occur as block copolymers of manuronic (M) and guluronic (G) acids and G-block oligomers can readily be produced from alginate source materials. Indeed, in general the oligouronate is preferably an oligoguluronic acid, or less preferably an oligogalacturonic acid.

Where alginates are used as the starting material for preparation of the oligouronate, the guluronic acid content may if desired be increased by epimerization with mannouronan C-5 epimerases from *A. vinelandii*.

Oligoguluronic acids suitable for use according to the invention may conveniently be produced by acid hydrolysis of alginic acid from *Laminaria hyperborea*, dissolution at neutral pH, addition of mineral acid to reduce the pH to 3.4 to precipitate the oligoguluronic acid, washing with weak acid, resuspension at neutral pH and freeze drying.

The use in medicine of oligouronates is itself novel and forms a further aspect of the invention. Viewed from this aspect the invention provides oligouronates, especially oligoguluronic or oligogalacturonic acids, for use in medicine. Use of oligouronates in drug delivery, e.g. to enhance drug uptake, forms a further aspect of the invention.

Viewed from a further aspect the invention also provides a pharmaceutical composition comprising a physiologically tolerable oligouronate together with a physiologically tolerable carrier or excipient, and preferably also a further physiologically tolerable mucosal viscosity reducing agent, e.g. a nucleic acid cleaving enzyme (e.g. a DNAse such as DNase I), gelsolin, a thiol reducing agent, an acetylcysteine, sodium chloride, an uncharged low molecular weight polysaccharide (e.g. dextran), arginine (or other nitric oxide precursors or synthesis stimulators), or an anionic polyamino acid (e.g. poly ASP or poly GLU). The use of a DNase is especially preferred. The oligouronate may be administered typically in doses of 1 to 10000 mg, especially 10 to 100 mg for an adult human. The optimum does may readily be determined by routine dosage ranging experiments, optionally following initial investigation of an animal model, e.g. a dog model.

The compositions of the invention may be produced using conventional pharmaceutical carriers and excipients, e.g. solvents (such as water), osmolality modifiers, flavours, pH regulators, etc. They may contain additional active components, for example agents which serve to break down biopolymers not involved in the mucin matrix of the mucus (e.g. DNase, particularly rhDNase), antibacterial agents, and anti-inflammatories. Combination therapy using a such further agent and the oligouronate, administered separately or together is a particularly preferred aspect of the method of the invention. Such further agents may be used in their normal doses or even at lower doses, e.g. 50% of normal dose.

The invention will now be described further with reference to the following non-limiting Examples and the accompanying drawings, in which:

FIGS. 1*a* to 1*f* are plots of complex modulus over time for a mucin-alginate gel and for the same gel dosed with dextran, polyethylene glycol, DNA, sodium galacturonate oligomer and sodium guluronate oligomer respectively;

EXAMPLE 1

The effect of five oligomeric materials on a model mucin-alginate gel were tested:—
a) Low molecular weight dextran (6000 Da)
b) Low molecular weight PEG (3350 Da)
c) Low molecular weight DNA
d) Sodium galacturonate oligomers
e) Sodium guluronate oligomers (G blocks)

The sodium guluronate oligomer was prepared as described above and had the following characteristics:

$F_G$ 0.87, $F_M$ 0.13, $F_{GG}$ 0.83, $F_{GM}=F_{MG}$ 0.05, $F_{MM}$ 0.08, $F_{GGM}=F_{MMG}$ 0.04, $F_{MGM}$ 0.02, $F_{GGG}$ 0.79, DP 19.

Materials

Control gel consisted of 18 mg/ml mucin+0.6 mg/ml alginate in 0.05M NaCl

Test gels consisted of 18 mg/ml mucin+0.6 mg/ml alginate+4 mg/ml test material in 0.05 M NaCl Rheological Tests Gelation—immediately after mixing the sample was loaded into the rheometer at 37° C. The temperature was cooled to 10° C. (0.5 degree/min) and then held at 10° C. for 18 hours. The behaviour of the sample and gel development was measured continuously.

Frequency sweep—after gelation the temperature of the sample was raised to 37° C. and the rheological behaviour monitored as a function of frequency.

Stress sweep—at 37° C., the behaviour of the gel was monitored as a function of increasing applied stress.

Gelation

The studies demonstrated that sodium guluronate oligomers (G blocks) are able to displace alginate in mucin—alginate interactions as seen by the decrease in the complex modulus of the gel (G*) over time after the initial gelation. For the five test gels and the control gel this is shown in FIGS. 1*a* to 1*f* respectively.

Of the other oligomeric materials tested only sodium galacturonate oligomers had a similar effect, showing a decrease in the moduli values over time. The other materials (DNA, PEG, dextran) caused a delay in gelation but the gel continued to develop over time as shown by the increase in complex modulus.

Figure 1A:
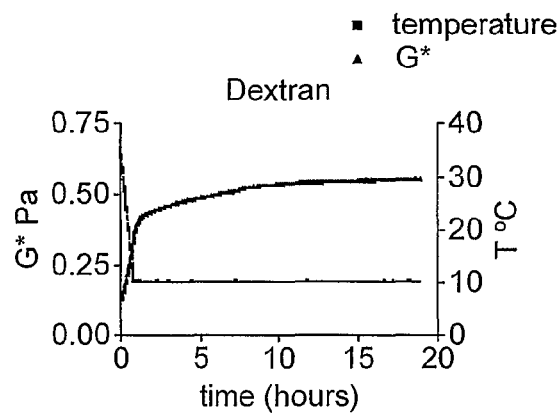
Figure 1C:
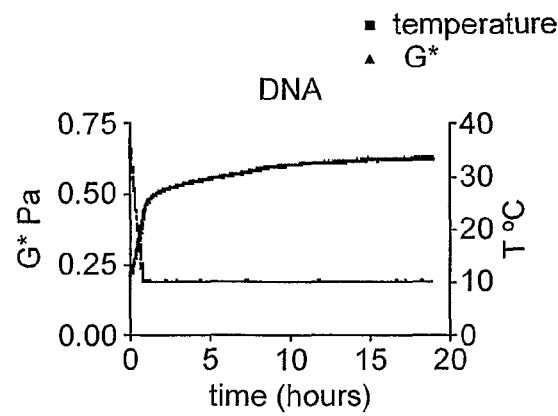
Figure 1B:
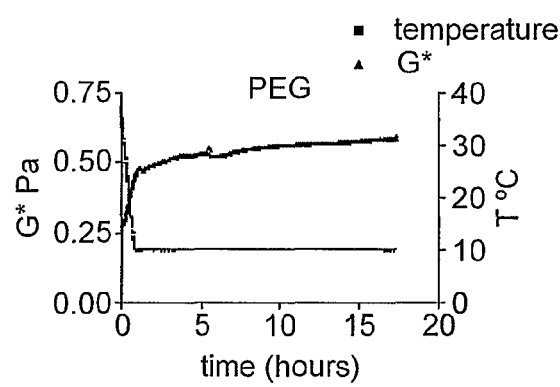
Figure 1D:
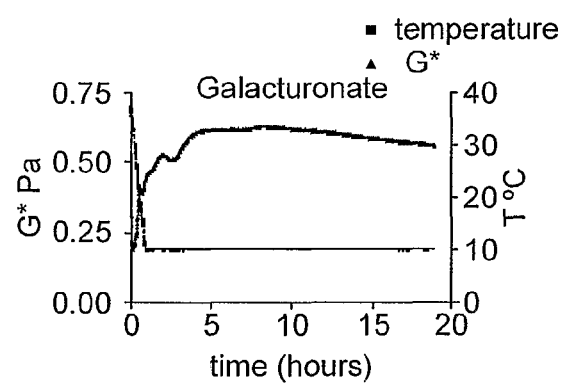
Figure 1F:
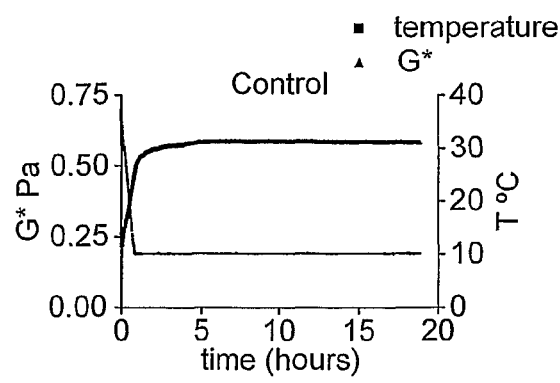
Figure 1E:
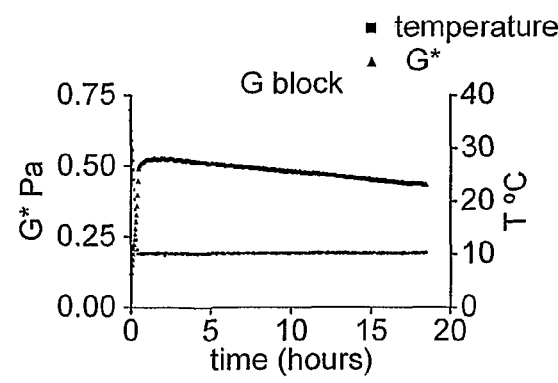
Figure 2:
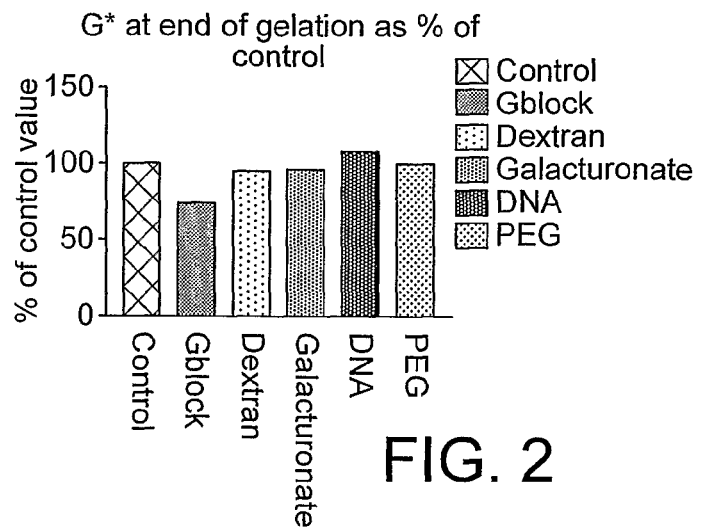
FIGS. 2 and 3 are bar charts showing the complex modulus (G*) and the phase angle of the same gels at the end of gelation as a percentage of the control.
Figure 3:
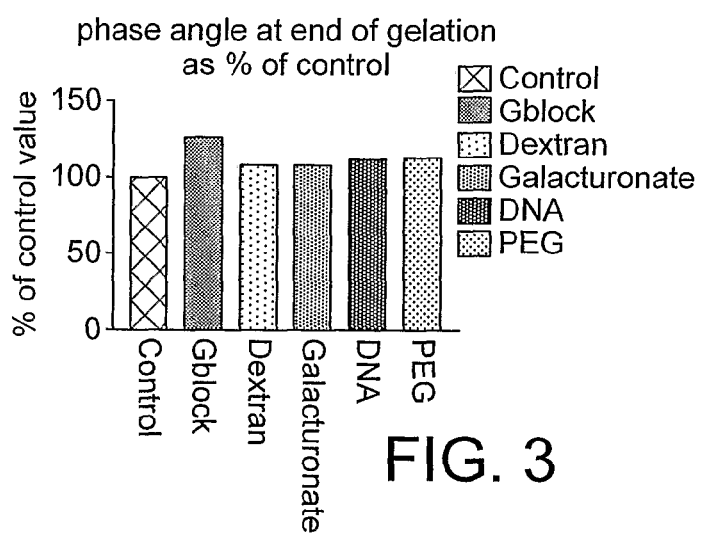

The complex modulus and phase angle of the gels at the end of the gelling period is plotted in FIGS. 2 and 3. The complex modulus is a measure of the total response or strength of the system and the phase angle concerns the balance between liquid like and solid like behaviour with a higher phase angle indicating greater liquid like behaviour. Sodium guluronate oligomers (G blocks) caused the greatest drop in G* and the greatest increase in the phase angle.

Gel Behaviour from the Frequency Sweep

All the gels showed frequency sweep behaviour typical of weak viscoelastic gels.

Flow Stress from the Stress Sweep

Figure 4:
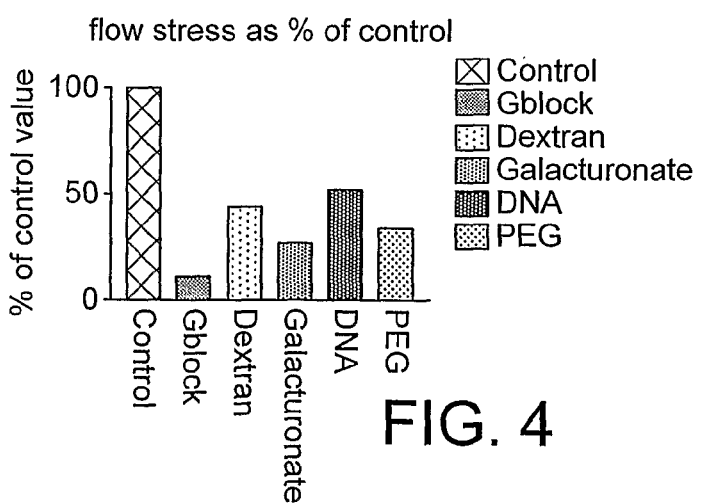
FIG. 4 is a bar chart showing the flow stress of the same gels, again as a percentage of the control.

A stress sweep was used to determine the stress needed to induce flow in the system. This is plotted in FIG. 4 as a % of the stress needed to induce flow in the control gel. This gives an indication of how much the added material has weakened the gel matrix. G blocks (sodium guluronate oligomers) had the most pronounced effect on the flow stress followed by sodium galacturonate oligomers.

EXAMPLE 2

Ferning

Mucin compositions were prepared as follows:
a) 18 mg mucin per mL 0.05M aqueous NaCl;
b) 18 mg mucin and 1 mg alginate per mL 0.05M aqueous NaCl; and
c) 18 mg mucin, 0.4 mg alginate, and 0.6 mg sodium guluronate oligomer (as in Example 1) per mL 0.05M aqueous NaCl.

Figure 5:
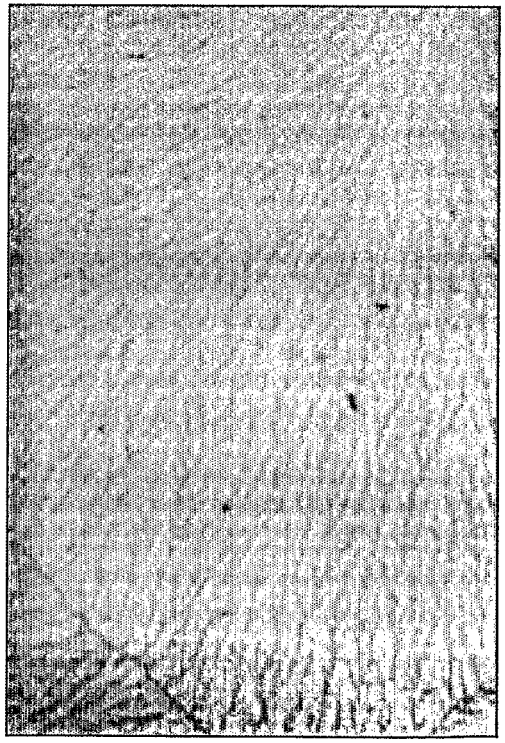
FIGS. 5*a* to 5*c* are photomicrographs of mucin untreated and treated with alginate and/or sodium guluronate oligomers.
Figure 5:
Figure 5:

The compositions were air dried and photomicrographs were recorded. These, at the same magnifications, are shown in FIGS. 5a to 5c for compositions (a) to (c) respectively.

It can clearly be seen that the guluronate oligomer promotes ferning.

EXAMPLE 3

Constipation Medicament

A 5-50 ml oral dose of an aqueous liquid consists of 5-30% of the sodium salt of a guluronic acid block with a purity of at least 75% guluronate and a degree of polymerisation between 5 and 20, and if necessary, a preservative agent. The liquid may also be combined with other compounds which have additional health benefits, e.g. vitamins.

The invention claimed is:

1. A method of treatment of a human or non-human subject to reduce mucosal hyperviscosity in the digestive tract, which method comprises applying to a mucosal surface of the digestive tract in said subject an amount of a physiologically tolerable oligouronate, wherein the amount is sufficient to reduce the mucosal hyperviscosity, and wherein said physiologically tolerable oligouronate is a linear 3- to 28-mer obtainable by polysaccharide lysis from an alginate.

2. The method as claimed in claim 1 for the treatment of constipation caused by mucosal hyperviscosity in the digestive tract.

3. The method as claimed in claim 1 wherein said oligouronate is administered orally or rectally.

4. The method as claimed in claim 1 wherein said oligouronate is an oligoguluronate.

5. The method as claimed in claim 1 wherein said oligouronate is a 4- to 25-mer.

6. The method of claim 1, wherein said oligouronate comprises at least 75% guluronate residues.

7. The method of claim 1, wherein said subject has cystic fibrosis.

8. A method of drug delivery for enhancing uptake of a drug, said method comprising administering to a mucus secreting or mucus carrying surface in the body of a patient a composition comprising the drug and an effective amount of a physiologically tolerable 3- to 28-mer oligouronate, wherein the composition does not contain ions that promote gelation, and wherein the oligouronate comprises at least 75% guluronic acid residues.

9. The method of claim 8, wherein said oligouronate is oligoguluronic acid.

10. The method of claim 8, wherein the composition does not contain group 2 metals.

* * * * *